United States Patent [19]

Merz et al.

[11] Patent Number: 4,932,955
[45] Date of Patent: Jun. 12, 1990

[54] CLIP

[75] Inventors: William Merz, Niles, Ill.; Albert L. Rhoton, Jr., Gainesville, Fla.

[73] Assignee: Baxter International Inc., Deerfield, Ill.

[21] Appl. No.: 626,300

[22] Filed: Jun. 29, 1984

[51] Int. Cl.⁵ .............................................. A61B 17/12
[52] U.S. Cl. ...................................... 606/158; 24/510
[58] Field of Search ............... 128/325, 346, 354, 326; 24/499, 500, 508, 510, 553; 606/157, 158

[56] References Cited

U.S. PATENT DOCUMENTS

| | | |
|---|---|---|
| 715,426 | 12/1902 | Schisgal . |
| 1,123,290 | 1/1915 | Von Herff . |
| 1,589,076 | 6/1926 | Haskins ............................. 24/508 X |
| 2,307,384 | 1/1943 | Bowen . |
| 2,876,778 | 3/1959 | Kees, Jr. . |
| 2,890,519 | 6/1959 | Storz, Jr. . |
| 3,126,005 | 3/1964 | Smialowski . |
| 3,518,993 | 7/1970 | Blake . |
| 3,598,125 | 8/1971 | Cogley . |
| 3,613,683 | 10/1971 | Kees, Jr. . |
| 3,805,792 | 4/1974 | Cogley . |
| 3,827,438 | 8/1974 | Kees, Jr. . |
| 4,112,951 | 9/1978 | Hulks et al. . |
| 4,192,315 | 3/1980 | Hilzinger et al. . |
| 4,242,902 | 1/1981 | Green . |
| 4,246,903 | 1/1981 | Larkin . |
| 4,274,415 | 6/1981 | Kanamoto et al. . |
| 4,324,248 | 4/1982 | Perlin . |
| 4,337,774 | 7/1982 | Perlin . |
| 4,340,061 | 7/1982 | Kees, Jr. et al. . |
| 4,360,023 | 11/1982 | Sugita et al. . |
| 4,367,746 | 1/1983 | Derechinsky . |
| 4,397,312 | 8/1983 | Molko . |
| 4,407,285 | 10/1983 | Perlin . |
| 4,416,266 | 11/1983 | Baucom . |
| 4,418,694 | 12/1983 | Beroff et al. . |
| 4,424,810 | 1/1984 | Jewusiak . |

FOREIGN PATENT DOCUMENTS

| | | |
|---|---|---|
| 136691 | 12/1902 | Fed. Rep. of Germany . |
| 2025868 | 12/1971 | Fed. Rep. of Germany . |
| 2647018 | 5/1977 | Fed. Rep. of Germany ...... 128/346 |
| 430945 | 8/1967 | Switzerland . |
| 1557682 | 12/1979 | United Kingdom . |
| 2119695 | 11/1983 | United Kingdom . |

OTHER PUBLICATIONS

Official Gazette, p. 585, Jul. 10, 1984. Spring Clip for Aneurysm Surgery, A. L. Rhoton, Jr. and W. Merz, Surg Neurol 1983; 19:14-6.

Primary Examiner—Michael H. Thaler
Attorney, Agent, or Firm—Leydig, Voit & Mayer

[57] ABSTRACT

The disclosure describes a clip which has particular application, for example, in the medical arts. The clip comprises a hollow, cylindrical hub which includes first and second hub sections defined by a plane transverse to the axis of the hub. A pin joins the first and second hub sections and allows them to rotate independently about the pin. First and second legs are joined to the first and second hub sections, respectively, each leg including a clamping surface. The clamping surface on the first leg opposes the clamping surface on the second leg. A spring mechanism biases the clamping surfaces together and includes first and second ends. A mechanism disposed on the first and second hub sections engages the first and second ends, respectively, of the spring, and a lever coupled to the first and second hub sections spreads the clamping surfaces apart.

17 Claims, 5 Drawing Sheets

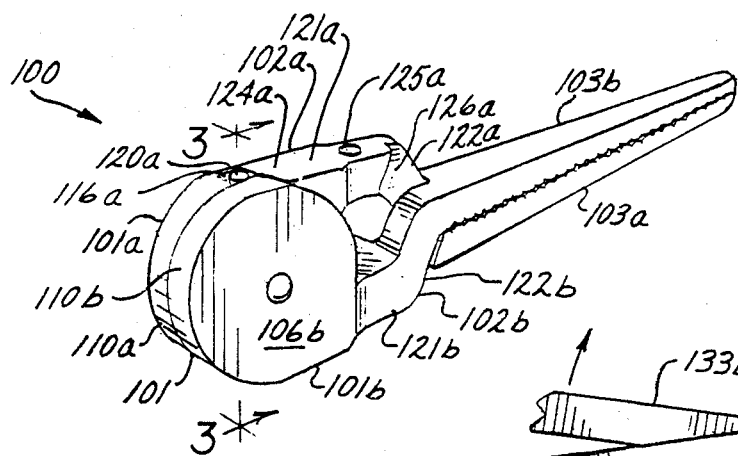
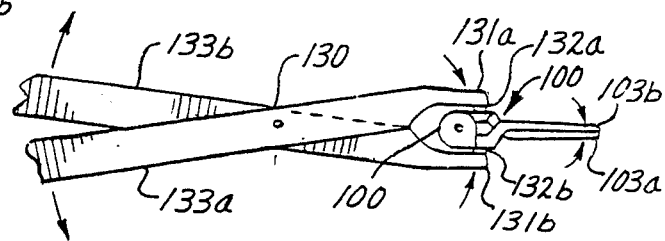
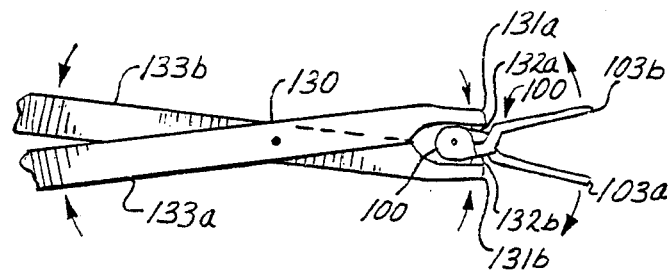
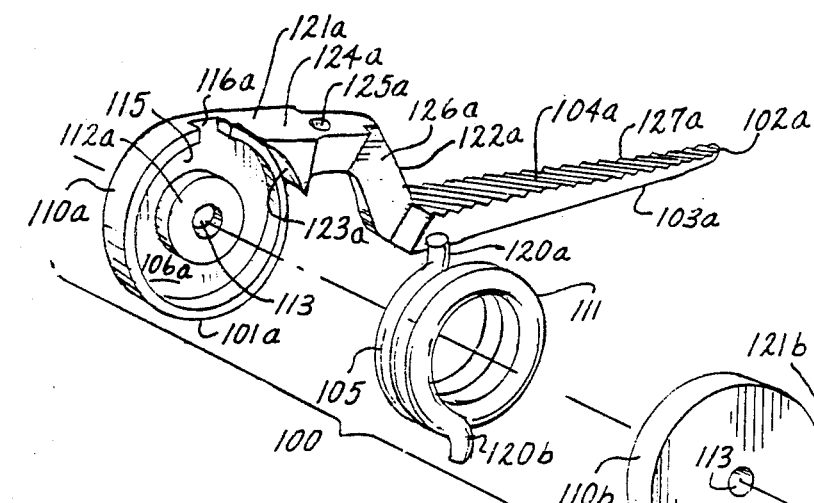

CLIP

Technical Field:

The present invention relates to a clip. In particular it relates to a clip which can be used, for example, in the medical arts.

Background Art:

Typically, a clip has two narrow projecting legs with opposed clamping surfaces and a spring that forces the clamping surfaces together. Such clips are widely used, for example, in the medical arts for clamping blood vessels and ducts. For example, it is common surgical practice to isolate an aneurysm, i.e., a weak, ballooned section of a blood vessel, by placing a clip across the neck of the ballooned aneurysm in order to isolate the aneurysm from the vessel on which it arose.

While previous clips have proven very effective for clamping off blood vessels and ducts, they, nonetheless, have several undesirable characteristics. For example, frequently the spring of the clip is partially or even totally exposed so that when the clip is placed within the body, tissue surrounding the clip can become enmeshed within the spring or between the spring and the legs of the clip. Removing the clip is then difficult, time consuming and dangerous since the tissue must be disentangled from the clip to avoid tearing it.

Another problem with previous clips is that the ends of the spring frequently move back and forth against the legs as the clamping surfaces are opened and closed. This movement between the ends of the spring and the legs can gall the legs, causing an uneven closing pressure. In some circumstances, it might even gouge small fragments from the legs which can contaminate a wound if they fall from the clip.

Disclosure Of The Invention:

The present invention provides an improved clip, e.g., a clip that not only prevents tissue from becoming enmeshed in the spring but also prevents galling between the spring and the legs of the clip. Accordingly, the present invention encompasses a clip comprising a hollow, cylindrical hub which includes first and second hub sections. The hub sections are joined by a pin that allows independent rotation of the hub sections about the pin. First and second legs are joined to the first and second hub sections, respectively, each leg including a clamping surface. The clamping surface of the first leg opposes the clamping surface of the second leg. A spring mechanism having first and second ends biases the clamping surfaces together. A mechanism disposed on the first and second hub sections engages the first and second ends, respectively, of the spring mechanism. First and second levers for spreading the clamping surfaces apart are respectively coupled to the first and second hub sections.

The present invention achieves each of the objects stated above. For example, in accordance with one aspect of the invention, the spring mechanism may be substantially entirely enclosed within the hollow, cylindrical hub, virtually eliminating the chance that any tissue will become enmeshed in the spring. In accordance with another aspect of the invention, the spring mechanism can include a coil spring with upturned ends, and each end can be disposed in a notch in a hub section. The ends of the spring then move with the hub sections, preventing any galling between the hub sections and the ends of the spring. Other objects, aspects and advantages will become apparent upon studying the following detailed description and the accompanying drawings of two preferred embodiments of the invention.

Brief Description Of The Drawings:

In the accompanying drawings:

FIG. 1 is a perspective view of a first aneurysm clip embodying the present invention;

FIG. 2 is a exploded perspective view of the aneurysm clip of FIG. 1;

FIG. 3 is a sectional view of the aneurysm clip of FIG. 1 as viewed along lines 3—3;

FIG. 4 is a side view of the aneurysm clip of FIG. 1 as opened by a clip applier;

FIG. 5 is a side view of the aneurysm clip of FIG. 1 as closed by a clip applier;

Figure 6:
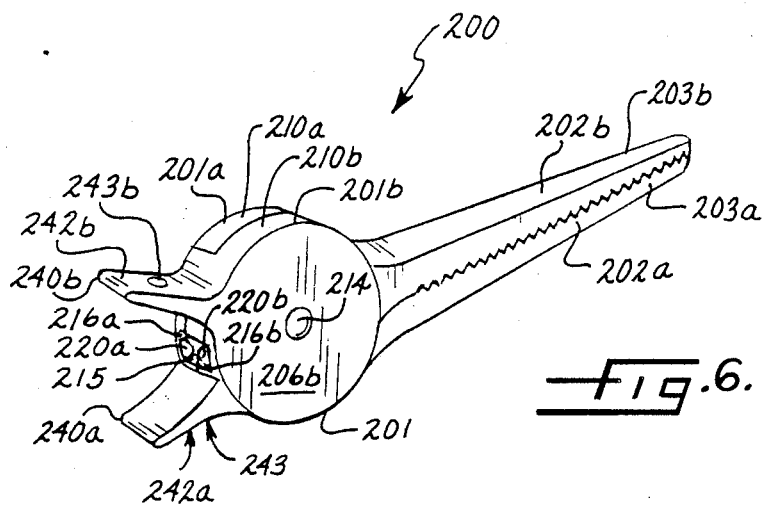
FIG. 6 is a perspective view of a second aneurysm clip embodying the present invention.

Best Mode For Carrying Out The Invention:

As shown in FIGS. 1–3, a first exemplary aneurysm clip 100 embodying the present invention comprises a hollow, generally cylindrical hub 101 and first and second legs 102a, 102b projecting in the same direction from spaced positions on the periphery of the hub 101. Each leg 102a, 102b includes a blade 103a, 103b with a clamping surface 104a, 104b for bearing against tissue. The aneurysm clip 100 also comprises a coil spring 105 for biasing the clamping surfaces 104a, 104b together.

In accordance with one aspect of the invention, the coil spring is contained entirely within the hollow hub 101. The hub 101 is divided in half along the transverse mid-plane of the hub 101, i.e., the mid-plane of the hub 101 perpendicular to the axis of the hub 101, forming first and second hub sections 101a, 101b. Each hub section 101a, 101b is the mirror image of the other and includes a generally circular hub plate 106a, 106b with a rim 110a, 110b that projects axially a short distance from the periphery of the hub plate 106a, 106b toward the other hub section 101b, 101a. The hub plates 106a, 106b and rims 110a, 110b serve to enclose the coil spring 105 and prevent tissue from becoming enmeshed between the spring 105 and the hub 101 or between the coils 111 of the spring 105.

To position the coil spring 105 and to lend additional structural support to the hollow hub 101, each hub section 101a, 101b also includes a cylindrical bushing 112a, 112b which projects coaxially from the hub plate 106a, 106b in the same direction and to the same extent as the rim 110a, 110b. A hole 113 extends coaxially through the bushing 112a, 112b and the hub plate 106a, 106b of each hub section 101a, 101b. A pin 114, which is disposed within the hole 113 and riveted in position, joins the hub sections 101a, 101b but leaves them free to rotate independently about the pin 114. The hub sections 101a, 101b are joined with their respective rims 110a, 110b and bushings 112a, 112b abutting, defining an annular space 115 within the hub 101. The coil spring 105 is disposed within this annular space 115 with the coils 111 of the spring 105 mounted about the cylindrical bushings 112a, 112b.

The first and second legs 102a, 102b project from the rims 110a, 110b of the first and second hub sections 101a, 101b, respectively, and the coil spring 105 is operatively coupled to each hub section 101a, 101b, opposing any rotation of the hub sections 101a, 101b which moves the clamping surfaces 104a, 104b apart. In accordance with another aspect of the invention, whenever the hub sections 101a, 101b rotate in opposite directions about the pin 114, there is no relative movement between the coil spring 105 and the hub sections 101a, 101b at the locations where the coil spring 105 is operatively coupled to the hub sections 101a, 101b. In the preferred embodiment, a notch 116a, 116b is formed in the rim 110a, 110b of each hub section 101a, 101b with the notch 116a, 116b in one rim 110a, 110b diametrically opposed to the notch 116b, 116a in the other rim 110b, 110a. The coil spring 105 terminates in upturned ends 120a, 120b, and each end 120a, 120b is disposed in a notch 116a, 116b, exerting a tangential force on the corresponding rim 110a, 110b. Since the coil spring 105 winds or unwinds as the hub sections 101a, 101b rotate in opposite directions about the pin 114 and, since the upturned ends 120a, 120b move ciucumferentially as the spring 105 winds or unwinds, there is no relative movement between the rim 110a, 110b and the upturned end 120a, 120b disposed in the notch 116a, 116b in the rim 110a, 110b, as with many conventional clips. Consequently, the ends 120a, 120b of the spring 105 do not gall against or gouge small fragments from the hub sections 101a, 101b.

Further, the upturned ends 120a, 120b of the spring 105 and the notches 116a, 116b in the hub sections 101a, 101b are dimensioned to minimize contact between the spring 105 and the environment outside the hub 101 and between the environment and the interior of the hub 101. Thus, the upturned ends 120a, 120b extend no further than the periphery of the rims 110a, 110b, and the notches 116a, 116b, though square, are no larger than necessary to accommodate the diameter of the spring wire. Consequently, the clip 100 presents no jagged projections or depressions which can tear or trap tissue.

While the notches 116a, 116b and the upturned ends 120a, 120b comprise the preferred mechanism for coupling the coil spring 105 to the hub 101, other mechanisms may be used without departing from the scope of the invention. For example, a protrusion projecting radially inwardly a short distance from each rim could be substituted for the notch in the rim. The upturned ends of the coil spring would then act against the protrusions, causing the hub sections to rotate in opposite directions, again without relative movement between the upturned ends and the protrusions.

The first and second legs 102a, 102b project from the hub sections 101a, 101b near the notches 116a, 116b in the rims 110a, 110b, each leg 102a, 102b extending through an initial member 121a, 121b and a cross-over member 122a, 122b before terminating in the blade 103a, 103b. The portion of each initial member 121a, 121b nearest the hub section 101a, 101b extends axially beyond the rim 110a, 110b for the full length of the hub 101, forming an arcuate lip 123a, 123b within which the rim 110b, 110a of the other hub section 101b, 101a fits. With the clamping blades 104a, 104b abutting, the initial members 121a, 121b project from the hub 101 symmetrically with respect to the transverse mid-plane and parallel to each other, each narrowing as it approaches the cross-over member 122a, 122b. Each initial member 121a, 121b has a surface 124a, 124b which is tangential to the hub 101 and which contains a conical depression 125a, 125b bisected by the transverse midplane.

The cross-over member 122a, 122b of each leg 102a, 102b lies only on one side of the transverse mid-plane, i.e., the same side as the hub section 101a, 101b from which the leg 102a, 102b projects, includes a broad surface 126a, 126b facing but spaced from the transverse mid-plane. The cross-over members 122a, 122b project from respective initial members 121a, 121b at an angle such that, when viewed orthogonally to the transverse mid-plane, they cross at a point proximate the blades 103a, 103b when the clamping surfaces 104a, 104b are abutting.

Lying symmetrically with respect to the transverse mid-plane, the blades 103a, 103b project from the cross-over members 122a, 122b at an angle such that both clamping surfaces 104a, 104b lie within the same axial mid-plane, i.e., a mid-plane of the hub 101 containing the axis of the hub 101, when the clamping surfaces 104a, 104b are abutting. The clamping surfaces 104a, 104b, which serve to compress and occlude, for example, the neck of an aneurysm, have fine serrations 127a, 127b running obliquely across the full width of the blade 103a, 103b to reduce slippage. Alternatively, the clamping surfaces 104a, 104b can include small, teeth-like projections instead of the fine serrations 127a, 127b.

The aneurysm clip 100 may be fabricated according to many known techniques. For example, according to a preferred technique, each hub section 101a, 101b and associated leg 102a, 102b may be milled from a piece of bar stock of, for example, rust-resistant stainless steel. Consequently, the stresses and structural weaknesses associated with the bends in many conventional aneurysm clips are avoided. The coil spring 105 may be drawn and shaped from spring wire in a conventional manner and is then fitted within one hub section 101a, 101b with the coils 111 mounted about the cylindrical bushing 112a, 112b and an upturned end 120a, 120b inserted into the notch 116a, 116b. The other hub section 101b, 101a and associated leg 102b, 102a are then fitted to the hub section 101a, 101b and associated leg 102a, 102b containing the coil spring 105 with the clamping surfaces 104a, 104b, rims 110a, 110b and bushings 112a, 112b abutting and the other upturned end 120b, 120a of the spring 105 inserted into the notch 116b, 116a. The pin 114 is then inserted into the hole 113 and riveted in place, yielding the aneurysm clip 100. Preferably several aneurysm clips 100 are fabricated having coil springs 105 of different tensions so that an aneurysm clip 100 having the optimal closing pressure may be selected for a particular application.

In the preferred mode of operation, the aneurysm clip 100 is grasped by a conventional clip applier 130 having opposed jaws 131a, 131b, each including opposingly directed projections 132a, 132b which fit into the depressions 125a, 125b in the initial members 121a, 121b of the legs 102a, 102b of the clip 100, as shown in FIG. 4. As the handles 133a, 133b of clip applier 130 are squeezed together, the jaws 131a, 131b approach each other and the projections 132a, 132b bear against the legs 102a, 102b, forcing the initial members 121a, 121b together. With the initial members 121a, 121b acting as levers rotating the hub sections 101a, 101b in opposite directions about the pin 114, the clamping surfaces 104a, 104b are spread apart. As the hub sections 101a, 101b rotate in opposite directions about the pin 114, the rims 110a, 110b of the hub sections 101a, 101b act against the upturned ends 120a, 120b of the spring 105, winding the spring 105 tighter. Since the upturned ends 120a, 120b of the spring 105 move circumferentially with the rims 110a, 110b, there is no relative movement between them and no galling or gouging as one piece of metal moves against another.

With the clamping surfaces 104a, 104b spread apart, the blades 103a, 103b are positioned, for example, with the neck of an aneurysm between them and the handles 133a, 133b of the clip applier 130 are spread, forcing the jaws 131a, 131b apart, as shown in FIG. 5. The upturned ends 120a, 120b of the coil spring 105, acting against the rims 110a, 110b then rotate the hub sections 101a, 101b in opposite directions about the pin 114 such that the clamping surfaces 104a, 104b close on the neck of the aneurysm. Again, as the hub sections 101a, 101b rotate, the upturned ends 120a, 120b of the spring 105 move circumferentially with the rims 110a, 110b without relative movement between them. Further, since the hub sections 101a, 101b and associated legs 102a, 102b have broad surface areas abutting one another, e.g., between the ends of the rims 110a, 110b and bushings 112a, 112b and between the rims 110a, 110b and the arcuate lips 123a, 123b, the clamping surfaces 104a, 104b are reliably maintained in opposition throughout the opening and closing of the blades 103a, 103b. Since the facing surfaces 124a, 124b are spaced from each other, a gap is maintained between them at all times while the blades 103a, 103b are opening and closing, preventing any "scissoring" of tissue by the cross-over members 122a, 122b.

Figure 7:
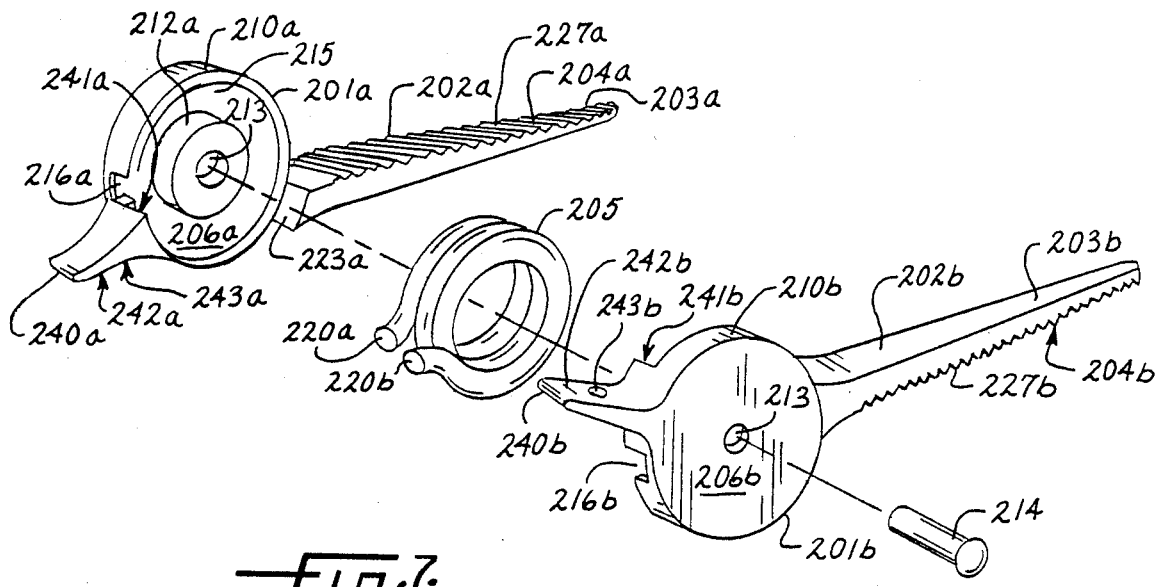
FIG. 7 is an exploded perspective view of the aneurysm clip of FIG. 6.

As shown in FIGS. 6 and 7, a second exemplary aneurysm clip 200 embodying the present invention also comprises a hollow, generally cylindrical hub 201, including first and second hub sections 206a, 206b, and first and second legs 202a, 202b projecting in the same direction from the periphery of the first and second hub sections 201a, 201b, respectively. As in the first aneurysm clip 100, each of the legs 202a, 202b also include a blade 203a, 203b with a clamping surface 204a, 204b for bearing against tissue, and a coil spring 205 biases the clamping surfaces 204a, 204b together. Each of the hub sections 201a, 201b includes a hub plate 206a, 206b, a rim 210a, 210b, cylindrical bushing 212a, 212b, and central hole 213, virtually identical to those of the first aneurysm clip 100. A pin 214 similarly joins the hub sections 201a, 201b, leaving them free to independently rotate and defining an annular space 215 within the hub 201. The coil spring 205 is, again, contained entirely within the annular space 215 of the hub 201 and coupled to the hub sections 201a, 201b at notches 216a, 216b into which upturned ends 220a, 220b of the spring 205 are inserted.

Unlike the first aneurysm clip 100, the notches 216a, 216b of the second aneurysm clip 200 are disposed in diametrically corresponding locations in the rims 212a, 212b. The legs 202a, 202b, which include only the blades 203a, 203b, radially project symmetrically with respect to the transverse mid-plane from locations on the rims 210a, 210b diametrically opposed to the notches 216a, 216b. The portion of each blade 203a, 203b nearest the rim 210a, 210b extends axially beyond the rim 210a, 210b for the full length of the hub 201, forming a lip 223a, 223b within which the other rim 210b, 210a fits. The clamping surfaces 204a, 204b of the second aneurysm clip 200 also have fine serrations 227a, 227b running obliquely across the full width of the blades 203a, 203b. Alternatively, the clamping surfaces 204a, 204b can include small, teeth-like projections instead of the fine serrations 227a, 227b.

Also unlike the first aneurysm clip 100, the second aneurysm clip 200 includes first and second spaced arms 240a, 240b which project radially from the rims 210a, 210b of the first and second hub sections 201a, 201b, respectively, proximate the notches 216a, 216b. The portion of each arm 240a, 240b nearest the rim 210a, 210b extends axially beyond the rim 210a, 210b for the full length of the hub 201, forming an arcuate lip 241a, 241b within which the other rim 210b, 210a fits. The arms 240a, 240b, which project from the hub 201 symmetrically with respect to the transverse mid-plane, include opposite facing surfaces 242a, 242b containing conical depressions 243a, 243b.

The second aneurysm clip 200 is preferably fabricated in a fashion identical to that of the first aneurysm clip 100, and the preferred mode of operation is very similar. The clip 200 is grasped in a clip applier with the projections of the clip applier fitting into the conical depressions 243a, 243b on the radial arms 240a, 240b. As the handles of the clip applier are squeezed together, the arms 240a, 240b on the hub 201 are forced together. With the arms 240a, 240b acting as levers rotating the hub sections 201a, 201b in opposite directions, the clamping surfaces 204a, 204b are spread apart. The rims 210a, 210b of the rotating hub sections 201a, 201b act against the upturned ends 220a, 220b of the spring 205, winding the spring 205 tighter. When the handles of the clip applier are spread, the upturned ends 220a, 220b of the spring 205 act against the rims 210a, 210b, rotating the hub sections 201a, 201b in opposite directions and closing the blades 203a, 203b. As in the first aneurysm clip 100, all interaction between the rims 210a, 210b and the up-turned ends 220a, 220b occurs without relative movement.

Although the present invention has been described in terms of two particular embodiments, it is not limited to these embodiments. Alternative embodiments and modifications which would still be encompassed by the invention may be made by those skilled in the art, particularly in light of the foregoing teachings. Therefore, the following claims are intended to cover any alternative embodiments, modifications or equivalents which may be included within the spirit and scope of the invention as defined by the claims.

What is claimed is:

1. An unplantable surgical clip comprising a hollow, cylindrical hub including first and second hub sections defined by a plane transverse to the axis of the hub; a pin joining the first and second hub sections for independent rotation about the pin; first and second legs joined to the first and second hub sections, respectively, each leg including a clamping surface, the clamping surface on the first leg opposing the clamping surface on the second leg; spring means substantially entirely enclosed with the hub for biasing the clamping surfaces together, the spring means including first and second end means; means disposed on the first and second hub sections for coupling the first and second end means to the first and second hub sections, respectively; and lever means coupled to the first and second hub sections for spreading the clamping surfaces apart.

2. The clip of claim 1 wherein the first and second end means of the spring means comprise first and second up-turned ends, respectively, and the coupling means comprises first and second apertures in the first and second hub sections, respectively.

3. The clip of claim 1 wherein each hub section comprises a generally circular plate and a rim extending axially from the periphery of the circular plate and wherein the coupling means is disposed on the rim of each hub section.

4. The clip of claim 3 wherein the coupling means comprises a notch disposed in each rim.

5. The clip of claim 4 wherein the spring means comprises a coil spring and the first and second end means comprise first and second upturned ends and wherein an upturned end is disposed in each notch.

6. The clip of claim 1 wherein each leg includes an initial member proximate the hub, a blade farthest from the hub, the blade including the clamping surface of the leg, and a cross-over member coupling the initial member to the blade, the cross-over members reversing the relative positions of the blades with respect to the relative positions of the initial members, and wherein the lever means comprises the initial members.

7. The clip of claim 1 wherein the lever means comprises first and second arms joined to the first and second hub sections, respectively, at locations circumferentially spaced from the legs and from each other along the periphery of the hub.

8. An implantable surgical clip comprising a hollow, cylindrical hub including first and second hub sections defined by a plane transverse to the axis of the hub; a pin joining the first and second hub sections for independent rotation about the pin; first and second legs joined to the first and second hub sections, respectively, at circumferentially spaced locations along the periphery of the hub, each leg including an initial member proximate the hub, a blade farthest from the hub, and a cross-over member coupling the initial member to the blade, wherein the blades include opposed clamping surfaces and wherein the cross-over members reverse the relative positions of the blades with respect to the relative positions of the initial members; a coil spring substantially entirely enclosed within the hub for baising the clamping surfaces together, the spring including first and second end means; and first and second means disposed on the first and second hub sections for engaging the first and second end means, respectively.

9. The clip of claim 8 wherein each hub section comprises a generally circular plate and a rim extending axially from the periphery of the circular plate and wherein the first and second engaging means are disposed on the rim of the first and second hub sections, respectively.

10. The clip of claim 9 wherein each engaging means comprises a notch disposed in the rim.

11. The clip of claim 10 wherein the first and second end means of the coil spring comprise first and second upturned ends and wherein an upturned end is disposed in each notch.

12. The clip of claim 11 wherein each of the initial members extend axially substantially the entire length of the hub.

13. An implantable surgical clip comprising a hollow, cylindrical hub including first and second hub sections defined by a plane transverse to the axis of the hub; a pin joining the first and second hub sections for independent rotation about the pin; first and second legs joined to the first and second hub sections, respectively, at circumferentially proximate locations along the periphery of the hub, each leg comprising a blade having a clamping surface, the clamping surface on the first leg opposing the clamping surface on the second leg; a coil spring substantially entirely enclosed within the hub for biasing the clamping surfaces together, the spring including first and second end means; first and second means disposed on the first and second hub sections for engaging the first and second end means, respectively; and first and second arms joined to the first and second hub sections, respectively, at locations circumferentially spaced from the legs and from each other along the periphery of the hub.

14. The clip of claim 13 wherein each hub section comprises a generally circular plate and a rim extending axially from the periphery of the circular plate and wherein the first and second engaging means are disposed on the rims of the first and second hub sections, respectively.

15. The clip of claim 14 wherein each engaging means comprises a notch in the rim.

16. The clip of claim 15 wherein the first and second end means of the coil spring comprise first and second upturned ends and wherein an upturned end is disposed in each notch.

17. The clip of claim 16 wherein the portion of the legs and arms proximate the hub extend axially substantially the entire length of the hub.

* * * * *

UNITED STATES PATENT AND TRADEMARK OFFICE
CERTIFICATE OF CORRECTION

PATENT NO. : 4,932,955
DATED : June 12, 1990
INVENTOR(S) : William Merz

It is certified that error appears in the above-identified patent and that said Letters Patent is hereby corrected as shown below:

Title page: item (19) Merz et al should read--Merz--.

Item [75] Inventors delete "Albert L. Rhoton, Jr.".

Column 6, line 46, change "unplantable" to --implantable--.
Column 6, line 55, change "with" to --within--.

Signed and Sealed this

Twenty-eighth Day of January, 1992

Attest:

HARRY F. MANBECK, JR.

*Attesting Officer*          *Commissioner of Patents and Trademarks*